US009662039B2

(12) United States Patent
Liu et al.

(10) Patent No.: US 9,662,039 B2
(45) Date of Patent: May 30, 2017

(54) SYSTEM AND METHOD FOR FUNCTIONAL BRAIN ORGANIZATION MAPPING

(71) Applicants: Hesheng Liu, Marblehead, MA (US); Danhong Wang, Belmont, MA (US); Michael D. Fox, Newton, MA (US)

(72) Inventors: Hesheng Liu, Marblehead, MA (US); Danhong Wang, Belmont, MA (US); Michael D. Fox, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 167 days.

(21) Appl. No.: 14/672,657

(22) Filed: Mar. 30, 2015

(65) Prior Publication Data

US 2015/0272468 A1 Oct. 1, 2015

Related U.S. Application Data

(60) Provisional application No. 61/972,829, filed on Mar. 31, 2014.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0042* (2013.01); *A61B 5/16* (2013.01); *A61B 5/4064* (2013.01); *A61B 5/742* (2013.01); *G01R 33/4806* (2013.01)

(58) Field of Classification Search
CPC ......... A61B 5/055; A61B 5/4064; A61B 5/16; A61B 5/0042; A61B 5/742
See application file for complete search history.

(56) References Cited

U.S. PATENT DOCUMENTS

2002/0042563 A1* 4/2002 Becerra ................. A61B 5/055
600/407
2002/0103429 A1* 8/2002 deCharms .............. A61B 5/055
600/410
(Continued)

OTHER PUBLICATIONS

Varoquaux et al., "Brain covariance selection: better individual functional connectivity models using population prior", Advances in Neural Information Processing Systems, 2010.
(Continued)

*Primary Examiner* — Bo J Peng
(74) *Attorney, Agent, or Firm* — Quarles & Brady LLP

(57) ABSTRACT

Systems and method for producing functional brain organization maps are provided. The method includes providing functional connectivity magnetic resonance image (fcMRI) data, a population atlas, a variation map indicative of inter-subject variability in the atlas. The method also includes initializing a subject map using the atlas, determining a reference signal for each functional connectivity network in the subject map using signals derived from the fcMRI data, computing correlations between the signals and reference signal of each functional connectivity network, and iteratively updating the subject map by reassigning locations in the subject brain when correlating with a functional connectivity network, updating at each iteration the reference signal using the subject map, the population atlas, the variation map, and the set of fcMRI data. The method further includes generating a report indicative of a functional brain organization for the brain of the subject using the subject map.

23 Claims, 4 Drawing Sheets

(51) Int. Cl.
*A61B 5/16* (2006.01)
*G01R 33/48* (2006.01)

(56) References Cited

U.S. PATENT DOCUMENTS

| | | | | |
|---|---|---|---|---|
| 2002/0193684 | A1* | 12/2002 | Anderson | A61B 5/055 600/411 |
| 2006/0036153 | A1* | 2/2006 | Laken | A61B 5/0476 600/410 |
| 2007/0019846 | A1* | 1/2007 | Bullitt | G06T 7/0014 382/128 |
| 2009/0157481 | A1* | 6/2009 | Jung | A61B 5/0476 709/205 |
| 2009/0318773 | A1* | 12/2009 | Jung | A61B 5/04009 600/300 |
| 2013/0123607 | A1* | 5/2013 | Leuthardt | A61B 5/0042 600/410 |
| 2014/0343399 | A1* | 11/2014 | Posse | A61B 5/055 600/410 |

OTHER PUBLICATIONS

Mueller et al., "Individual Variability in Functional Connectivity Architecture of the Human Brain", Neuron 77, 585-595, Feb. 6, 2013.

* cited by examiner

SYSTEM AND METHOD FOR FUNCTIONAL BRAIN ORGANIZATION MAPPING

CROSS REFERENCE TO RELATED APPLICATIONS

This application claims the benefit of U.S. Provisional Patent Application Ser. No. 61/972,829, filed on Mar. 31, 2014, and entitled "SYSTEM AND METHOD FOR FUNCTIONAL BRAIN ORGANIZATION MAPPING."

STATEMENT REGARDING FEDERALLY SPONSORED RESEARCH

This invention was made with government support under NS069805 awarded by the National Institutes of Health. The government has certain rights in the invention.

BACKGROUND

The present disclosure relates generally to systems and methods for magnetic resonance imaging and, in particular, to systems and methods for functional brain mapping.

Neurosurgical procedures for patients with brain afflictions often require a balance between minimizing post-operative functional deficits and maximizing the benefits of the intervention. Each year, about 200,000 people are diagnosed with primary or metastatic brain cancer, with an approximate 0.6% lifetime risk, where the best hope for survival includes maximizing tumor resection while preserving as much normal functioning brain as possible. Epilepsy is another common disease affecting about 0.7% of the population, with about a third of the cases amenable to surgical treatment. To avoid post-surgical morbidity, routine surgical planning is typically associated with a process for obtaining the functional organization of brain. This involves several major difficulties, including determining the dominant hemisphere for the identification of important functions, mapping healthy eloquent cortices, and localizing epileptic foci or defining borders for brain lesions.

Information about the anatomical relationship between eloquent cortex and an area to be excised is extremely valuable in planning the operation. For example, in patients with frontal or parietal lobe lesions, it is often important to map the proximity or involvement of the primary motor and sensory cortices. Also, in frontal and temporal epilepsy patients, mapping language and memory systems is usually required. To map the eloquent cortices, invasive cortical stimulation is often managed peri-operatively in the awake patient or in the pre-surgical patient with subdural grids implanted. Under these conditions, stimulation-induced disruption provides information about the location of eloquent cortex. With subdural grids, it is also possible to conduct evoked potential studies to identify the functional networks. Although cortical stimulation can accurately map many functional systems, it is far from perfect. Besides the common drawbacks of all invasive techniques, cortical mapping usually occurs a short time before the planned resection, leaving little time to analyze the results and discuss options. It also lacks of information about deep brain structures because the subdural grids only record the electrical potential on the brain surface. When language and memory functions are considered, patient participation is required.

More recently, fMRI has been offered as a non-invasive means of mapping eloquent cortices. The basic approach involves an imaging session while a patient performs a task set designed to target a single domain such as language, memory, or motor function. The obtained images are then used prior to the surgery to identify regions of functional activity. The approach is powerful because it allows detailed assessment of functional anatomy in a timely manner that includes deep brain structures. However, there are significant limitations. First, some patients have difficulty performing the required tasks, especially those who have developmental brain disorders, altered levels of consciousness or other functional impairments. If a patient is not able to perform the prescribed task, then functional mapping may be unreliable or prove impossible. Second, specific task sets must be performed to target distinct functions (e.g., language versus motor function). While optimization is possible to allow efficient cycling through multiple functional domains, it is presently not possible to simultaneously map multiple brain functions. Even within the motor system, task epochs must alternate between separate motor acts (e.g., hand versus tongue movements) to map their distinct anatomic locations.

Therefore, given the above limitations, there is a need for systems and methods for robust determination of a functional organization for an individual brain.

SUMMARY

The present invention overcomes the aforementioned drawbacks by providing systems and method directed to identifying the functional organization of an individual subject using resting state or task-based functional connectivity magnetic resonance imaging (fcMRI) data. In particular, the present invention makes use of fcMRI data in an approach that determines functional brain organization of the subject using information derived from a population of subjects. Specifically, an iterative algorithm is implemented, which employs a population atlas, identifying a functional network organization of the population, and variation map indicative of inter-subject variability in the functional networks of the population atlas.

In accordance with one aspect of the disclosure, a method for producing functional brain mapping of a subject is provided. The method includes providing a set of time-series functional connectivity magnetic resonance image (fcMRI) data acquired from a subject, providing a population atlas that associates locations in a population brain to a plurality of functional connectivity networks, the population brain representing a population of subjects, and providing a variation map indicative of inter-subject variability in the population atlas. The method also includes initializing a subject map using the population atlas, the subject map having locations in a brain of the subject that are assigned to the functional connectivity networks of the subject map, determining a reference signal for each functional connectivity network in the subject map using time-series signals derived from the set of time-series fcMRI data and computing a plurality of correlation values between the time-series signals and the reference signal of each functional connectivity network. The method further includes updating the subject map, using the correlation values, by reassigning locations in the subject brain when correlating with a functional connectivity network, and updating the reference signal for each functional connectivity network using the subject map, the population atlas, the variation map, and the set of fcMRI data. The method yet further includes iteratively repeating the steps of computing the correlation values, updating the subject map and updating the reference signal, until a stopping criterion is satisfied. The method yet further includes generating a report indicative of a functional brain organization for the brain of the subject using the subject map.

In accordance with another aspect of the disclosure, a system for producing functional brain mapping of a subject is provided. The system includes an input configured to receive a set of time-series functional connectivity magnetic resonance image (fcMRI) data acquired from a subject, receive a population atlas that associates locations in a population brain to a plurality of functional connectivity networks, the population brain representing a population of subjects, and receive a variation map indicative of inter-subject variability in the population atlas. The system also includes at least one processor configured to initialize a subject map using the population atlas, the subject map having locations in a brain of the subject that are assigned to the functional connectivity networks of the subject map, determine a reference signal for each functional connectivity network in the subject map using time-series signals derived from the set of time-series fcMRI data, and compute a plurality of correlation values between the time-series signals and the reference signal of each functional connectivity network. The at least one processor is also configured to update the subject map, using the correlation values, by reassigning locations in the subject brain when correlating with a functional connectivity network, and update the reference signal for each functional connectivity network using the subject map, the population atlas, the variation map, and the set of fcMRI data. The at least one processor is further configured to iteratively repeat the steps of computing the correlation values, updating the subject map and updating the reference signal, until a stopping criterion is satisfied, and generate a report indicative of a functional brain organization for the brain of the subject using the subject map. The system further includes an output configured for displaying the report.

In accordance with another aspect of the disclosure, a magnetic resonance imaging (MRI) system for producing functional brain mapping of a subject is provided. The system includes a magnet system configured to generate a polarizing magnetic field about at least a portion of a subject arranged in the MRI system, a plurality of gradient coils configured to apply a gradient field to the polarizing magnetic field, and a radio frequency (RF) system configured to apply a RF excitation field to a brain of the subject, and acquire therefrom a set of time-series functional connectivity magnetic resonance image (fcMRI) data. The MRI system also includes at least one computer configured to receive a population atlas that associates locations in a population brain to a plurality of functional connectivity networks, the population brain representing a population of subjects, and receive a variation map indicative of inter-subject variability in the population atlas. The at least one computer is also configured to initialize a subject map using the population atlas, the subject map having locations in a brain of the subject that are assigned to the functional connectivity networks of the subject map, determine a reference signal for each functional connectivity network in the subject map using time-series signals derived from the set of time-series fcMRI data, and compute a plurality of correlation values between the time-series signals and the reference signal of each functional connectivity network. The at least one computer is further configured to update the subject map, using the correlation values, by reassigning locations in the subject brain when correlating with a functional connectivity network, update the reference signal for each functional connectivity network using the subject map, the population atlas, the variation map, and the set of fcMRI data, and iteratively repeat the steps of computing the correlation values, updating the subject map and updating the reference signal, until a stopping criterion is satisfied. The at least one computer is further configured to generate a report indicative of a functional brain organization for the brain of the subject using the subject map.

The foregoing and other advantages of the invention will appear from the following description.

DETAILED DESCRIPTION

Figure 1:
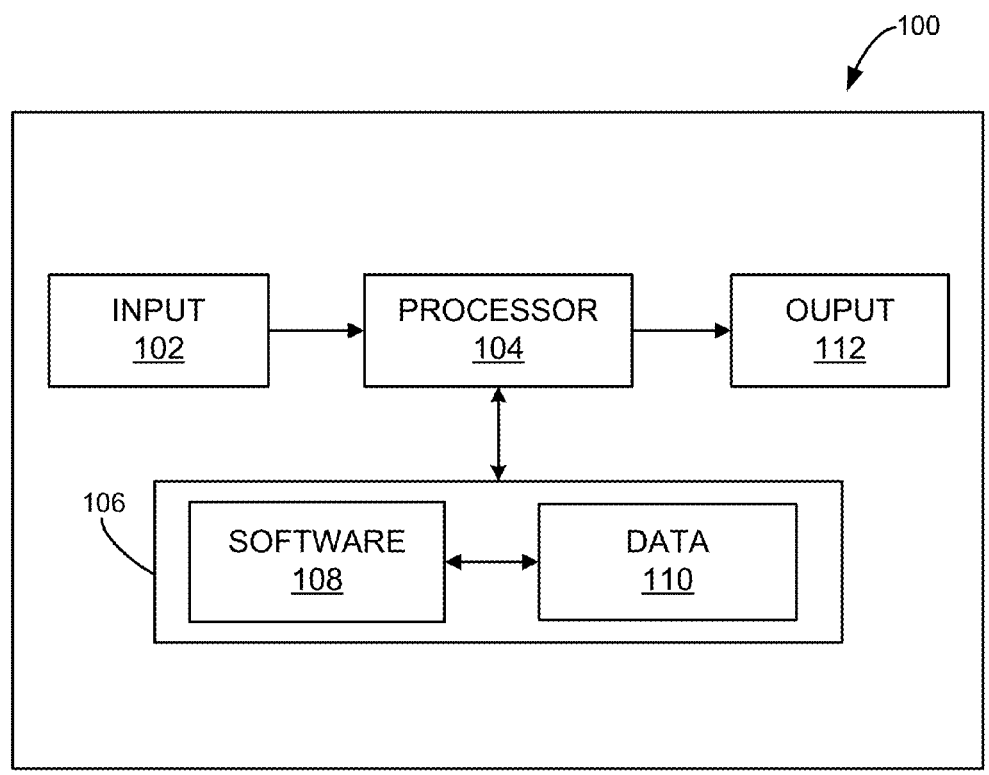
FIG. 1 is a block diagram is shown of an exemplary brain mapping system, for use in accordance with the present invention.

Functional imaging procedures can be used to map brain structure in quiet, resting-state subjects, and to explore the topography of brain systems using intrinsic functional connectivity magnetic resonance imaging (fcMRI). Such methods take advantage of spontaneous brain activity events that cascade through all brain systems and thus provide insight into the normally functioning brain as well as the abnormalities due to brain diseases. Described here are systems and methods that provide an approach that makes use of functional connectivity information to determine the functional lateralization of a subject's brain. The systems and methods described here are also capable of generating a comprehensive map of necessary eloquent cortex and brain abnormalities in surgical patients, which can be utilized for testing the clinical effectiveness of this non-invasive neuroimaging method.

Functional brain organization of each individual subject can be determined based on resting-state or task-based functional MRI data using an iterative adjusting approach. Examples of task-based functional MRI data include functional MRI data acquired while the subject performed a functional task, which may include a motor task, a language task, a visual task, and so on. The iterative optimization process described here is guided by a population-based functional atlas. In many instances, the influence of the population atlas on individual brain parcellation may not be the same for every subject or every brain region. To address these discrepancies, the systems and methods described here can flexibly determine the influence of the population atlas on a particular subject's brain parcellation by using an inter-subject variability map pre-estimated in the population. In some embodiments, the signal-to-noise distribution of the individual subject's data can also be used to this end. As an example, in some embodiments a weighting strategy is applied where the population atlas is weighted to have less impact on brain regions known to have a high level of inter-subject variability, or brain regions showing good SNR in a specific subject. In these regions, information extracted from the individual subject's data would be valued more than the population atlas. The details of the iterative optimization process are described below.

As will be described in greater detail below, the systems and methods of the present invention are capable of parcellating the functional networks in individual subject's brain based on fcMRI data using an iterative adjusting approach. As one non-limiting example, the technique generally includes the following steps. A population-based functional atlas is projected to an individual subject's brain. Mean time course of each network can then be extracted from the projected data for the individual subject's brain. These atlas-based network time courses can be used as the reference signals for the subsequent optimization procedure. The network membership of each brain vertex can then be reassigned according to its maximal correlation to the reference signals. A confidence value can also be computed for each vertex as the ratio between the largest correlation value and the second largest correlation. In the updated networks, time courses of the high confidence vertices in each network can be averaged and can serve as the individual-based network signal for the next iteration.

A new reference signal can be constructed for each network based on the individual-based network signal and the atlas-based network signal. Multiple weighting parameters, including a pre-estimated inter-subject variability, the normalized SNR value, and the number of iteration can be applied to both individual-based and atlas-based network signals. The weighting strategy ensures that atlas-based signals are less weighted in regions of high inter-subject variability and regions of high SNR, and also less weighted as the iteration number increases. The steps described above are repeated until the solution converges. In some embodiments, the algorithm is considered to be converged if network membership remains the same for 99% of the vertices in two consecutive iterations.

Turning to FIG. 1, a block diagram of an example system 100 that can be used for producing functional brain mapping of a subject is illustrated. The system 100 generally may include an input 102, at least one processor 104, a memory 106, an output 108, and any device for reading computer-readable media (not shown). The system 100 may be, for example, a workstation, a notebook computer, a personal digital assistant (PDA), a multimedia device, a network server, a mainframe or any other general-purpose or application-specific computing device. The system 100 may operate autonomously or semi-autonomously, or may read executable software instructions from a computer-readable medium (such as a hard drive, a CD-ROM, flash memory and the like), or may receive instructions from a user, or any another source logically connected to a computer or device, such as another networked computer or server, via the input 102.

The input 102 may take any shape or form, as desired, for operation of the system 100, including the ability for selecting, entering or otherwise specifying parameters consistent with operating the system 100. In some aspects, the input 102 may be designed to accept functional brain connectivity information describing a population of subjects. In particular, the input 102 may be configured to receive a population atlas that associates locations, or vertices, in a population brain to a plurality of functional networks, where the population brain is a combined representation of a population of subjects. For example, the population atlas may include parcellation maps illustrative of a number of different functional networks, or functionally-coupled regions, included in any portion of the population brain, such as the cerebral cortex. The input 102 may also be configured to receive a variation map indicative of inter-subject variability in the population atlas. In addition, the input 102 may further be configured to receive individual subject data, such as time-series functional magnetic resonance image (fMRI) data obtained from the subject in a resting state or while the subject performed a functional task. Such data may be pre-processed, filtered and corrected using known methods and technologies.

Among the processing tasks for operating the system 100, the at least one processor 104 may also be configured to receive the population atlas, variation map and time-series fMRI data, wherein the received time-series fMRI data may be pre-processed, and/or may undergo any number of further processing steps using the at least one processor 104. In some aspects, the at least one processor 104 may be capable of performing computations using time-series signals derived from time-series fMRI data. For example, the at least one processor 104 may be capable of combining any time-series signals associated with brain locations assigned to specific functional networks, or may be capable of correlating time-series signals in relation to any functional connectivity networks.

In other aspects, the at least one processor 104 may also be configured to perform iterative steps in a process for obtaining one or more subject maps for any one or more individuals, where the subject maps are illustrative of a functional brain organization of the individual subjects. Specifically, such iterative process, as will be described, may be guided by population information, such as organization and variability in functional networks of a population, as well as individual subject information, such as a signal-to-noise ratio determined from time-series fMRI data acquired from that subject.

The memory 106 may contain software 108 and data 110, and may be configured for storage and retrieval of processed information and data to be processed by the processor 104. In some aspects, the software 110 may contain instructions directed to performing an iterative process for obtaining subject map(s) representing functional brain organization of any individual subject(s), as mentioned. The data 112 may take include any data necessary for operating the system 100, and may include any raw or processed information in relation to a population atlas, variation map, time-series fMRI data, and subject map(s).

In addition, the output 112 may take any shape or form, as desired, and may be configured for displaying, in addition to other desired information, any information in relation to a population atlas, variation map, time-series fMRI data, and subject maps.

Figure 2:
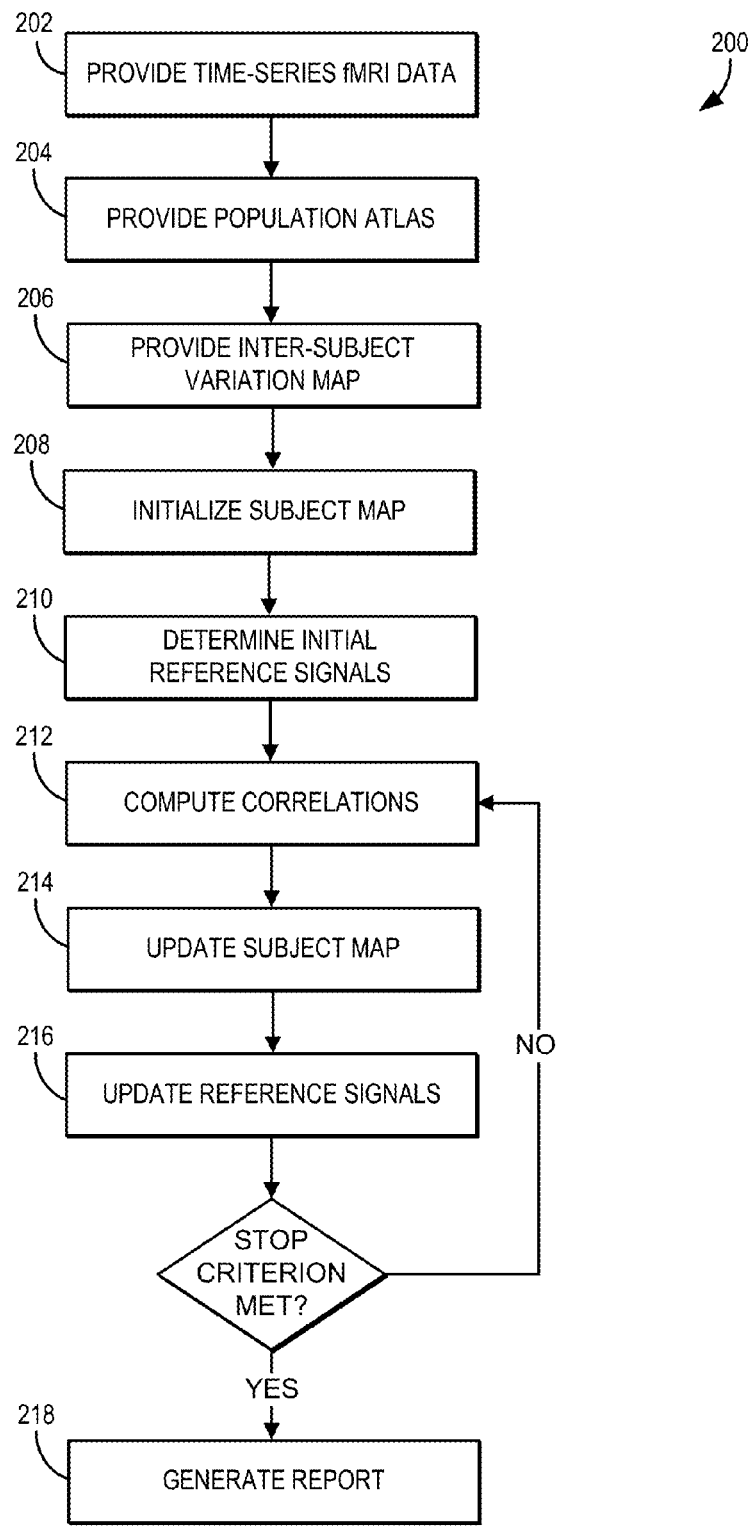
FIG. 2 is a flowchart setting forth steps of an example brain mapping method in accordance with the present invention.

Turning to FIG. 2, an example process 200 is illustrated setting forth steps of a method in accordance with some embodiments of the present invention. The process 200 may begin at process block 202, wherein time-series fMRI data is provided. In some aspects, this step may also include acquiring a set of time-series fMRI data using a magnetic resonance imaging (MRI) system. In some embodiments, this fMRI data may be indicative of a resting state of the subject. In some other embodiments, this fMRI data may be task-based fMRI data that is indicative of the subject performing a particular functional task. At process block 204, a population atlas is also provided. The population atlas generally associates locations, or vertices, in an average of brains in the population to a plurality of different functional networks. The average of the brains in the population is a combined representation of functional connectivity organization for the population of subjects that contributed to the population atlas. At process block 206, a variation map, indicative of inter-subject variability in the population atlas, is further provided. Although process blocks 202-206 are described in a specific order in FIG. 2, they may be carried out in any order, or in any concurrent combination.

Figure 3:
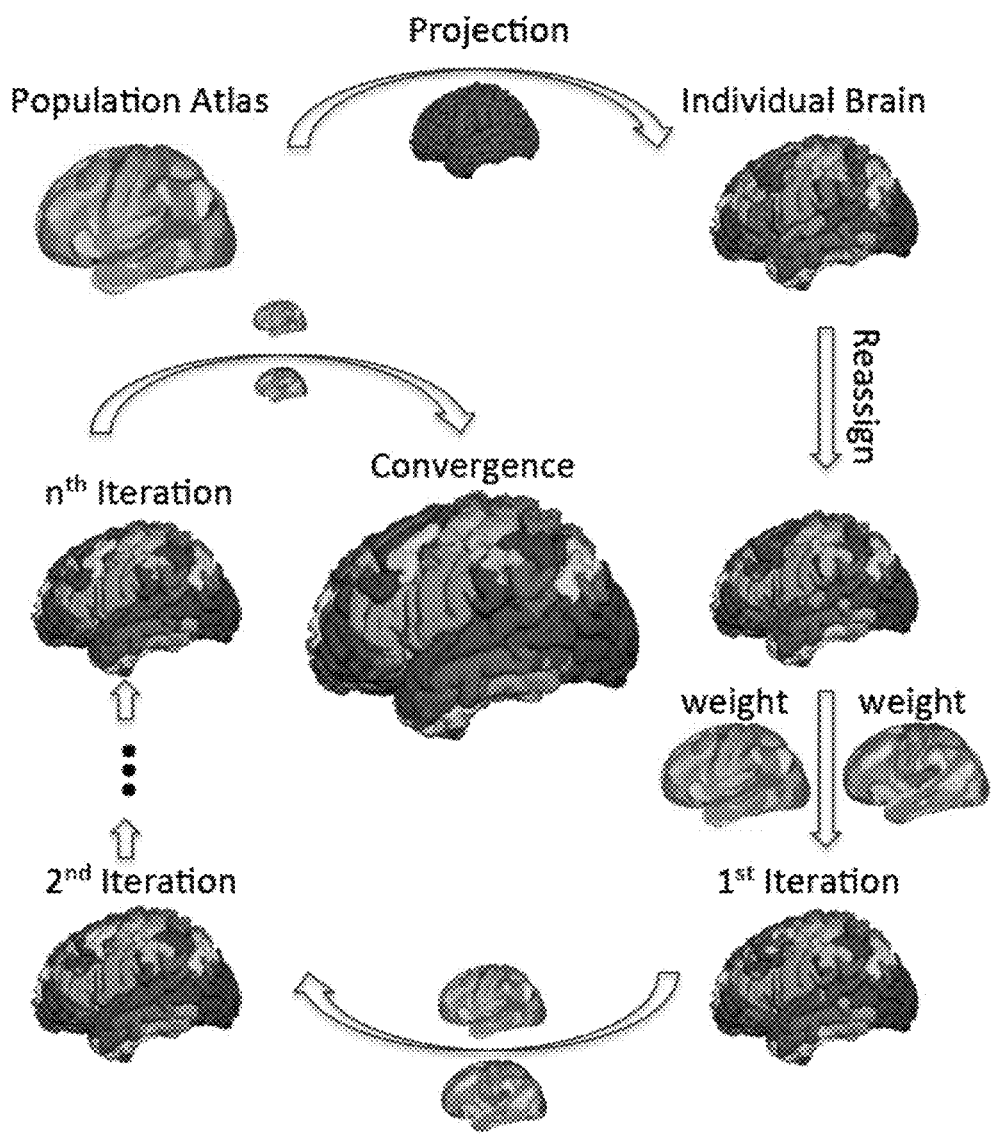
FIG. 3 is a schematic of an iterative process to determine an individual brain functional network map using population and individual-derived information.

At process block 208, a subject map is initialized. In some embodiments, this step involves projecting the population atlas onto an individual subject's brain surface, as illustrated in FIG. 3, using any systems, software or methods configured to do so. In this manner, the population atlas may serve as an initial guess of the functional network organization of the individual subject's brain. The subject map thus associates locations in the subject's brain with a plurality of different functional networks, such as those functional networks projected from the population atlas onto the surface of the individual subject's brain. Then at process block 210, a number of initial reference signals are determined in dependence of the number of functional networks in the subject map. Specifically, time-series signals derived from the resting-state fMRI data, and corresponding to locations, or vertices, in the subject brain, are averaged within each functional connectivity network. Thus, the averaged time course for each functional connectivity network in the subject map may be used as an initial reference signal for that network in a subsequent step.

At process block 212 correlations are computed between the time-series signals and each reference signal. In this step, a number of confidence values may be computed for each location, or vertex, where each confidence value is obtained from a ratio between the largest correlation value and the second largest correlation value. For example, if a vertex has the strongest correlation with the language network with a correlation coefficient of 0.8, and has the second strongest correlation with the motor network with a correlation coefficient of 0.4, then the confidence that this vertex belongs to the language network is 0.8/0.4=2. Then at process block 214, the subject map is updated through a reassignment process, wherein brain locations, or vertices, may be reassigned to different functional connectivity networks according to the correlation between their corresponding time-series signal and the most current reference signal extracted from each functional network. Specifically, a location, or vertex, may be reassigned to a specific functional connectivity network if it has the maximal correlation with the reference signal of this network compared to all other networks.

At process block 216, the reference signal of each functional connectivity network is then updated. This step involves using an average of time-series signals representing vertices recently assigned to the network. In some embodiments, when determining each updated reference signal, it may be desirable to average only the time-series signals of those locations, or vertices, that have high confidence. As an example, only those time-series signals at locations having a confidence value greater than 1.3 may be averaged; although, threshold values other than 1.3 are possible. In some embodiments, the updated reference signal also includes an additive component from the reference signal computed using the population-atlas. As an example, this additive component may be computed, per location or vertex, by taking the time-series signal of each vertex is divided by the inter-subject variability value, the normalized signal-to-noise ratio (SNR) for that vertex, and a number of the current iteration.

Using the updated reference signals from process block 216, which incorporate both the individual subject's information and the information provided by the population atlas, the process may be repeated by returning to process block 212, in dependence of a stopping criterion. Specifically, the iteration may cease when a convergent solution is achieved.

As one example, a convergent solution may be achieved when a certain percent of functional connectivity network membership remains the same in consecutive iterations, such as when 99% of the locations, or vertices, remain in the same functional network in consecutive iterations. As such, the subject map is progressively modified at process block 214 using a gradually increasing weighting of information from the individual brain while relaxing the constraints of the population-based parcellation. As may be appreciated, the approach of updating the reference signals in dependence of inter-subject variability, SNR and iteration number ensures that the population atlas has a minimal impact on brain regions of high individual variability, or high SNR, and its influence is gradually reduced with each iteration.

Finally, at process block 218, using the subject map, a report of any suitable shape or form is generated. As one example, the report may be indicative of a functional brain organization for the brain of the subject. For example, a generated report may be in the form of two or three-dimensional map, indicating the arrangement of functional connectivity networks in relation to anatomical features, portions or perspectives of the brain of an individual subject.

Figure 4:
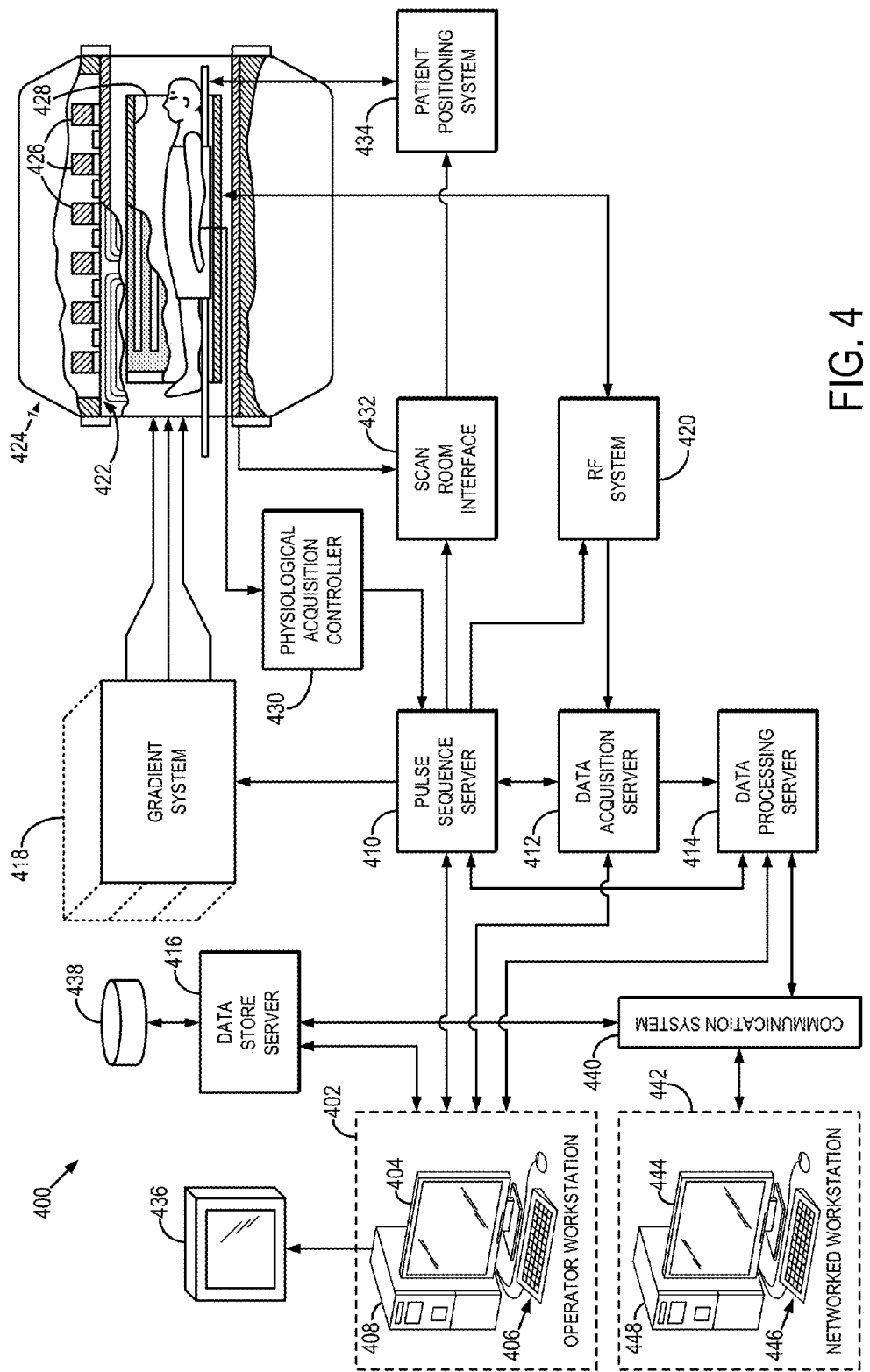
FIG. 4 is a block diagram of an example of a magnetic resonance imaging ("MRI") system.

Referring particularly now to FIG. 4, an example of a magnetic resonance imaging ("MRI") system 400 is illustrated. The MRI system 400 includes an operator workstation 402, which will typically include a display 404; one or more input devices 406, such as a keyboard and mouse; and a processor 408. The processor 408 may include a commercially available programmable machine running a commercially available operating system. The operator workstation 402 provides the operator interface that enables scan prescriptions to be entered into the MRI system 400. In general, the operator workstation 402 may be coupled to four servers: a pulse sequence server 410; a data acquisition server 412; a data processing server 414; and a data store server 416. The operator workstation 402 and each server 410, 412, 414, and 416 are connected to communicate with each other. For example, the servers 410, 412, 414, and 416 may be connected via a communication system 440, which may include any suitable network connection, whether wired, wireless, or a combination of both. As an example, the communication system 440 may include both proprietary or dedicated networks, as well as open networks, such as the internet.

The pulse sequence server 410 functions in response to instructions downloaded from the operator workstation 402 to operate a gradient system 418 and a radiofrequency ("RF") system 420. Gradient waveforms necessary to perform the prescribed scan are produced and applied to the gradient system 418, which excites gradient coils in an assembly 422 to produce the magnetic field gradients $G_x$, $G_y$, and $G_z$ used for position encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil (not shown in FIG. 4), in order to perform the prescribed magnetic resonance pulse sequence. Responsive magnetic resonance signals detected by the RF coil 428, or a separate local coil (not shown in FIG. 4), are received by the RF system 420, where they are amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the scan prescription and direction from the pulse sequence server 410 to produce RF pulses of the desired frequency, phase, and pulse amplitude waveform. The generated RF pulses may be applied to the whole-body RF coil 428 or to one or more local coils or coil arrays (not shown in FIG. 4).

The RF system 420 also includes one or more RF receiver channels. Each RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 410 also optionally receives patient data from a physiological acquisition controller 430. By way of example, the physiological acquisition controller 430 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, such that no data is lost by data overrun. In some scans, the data acquisition server 412 does little more than pass the acquired magnetic resonance data to the data processor server 414. However, in scans that require information derived from acquired magnetic resonance data to control the further performance of the scan, the data acquisition server 412 is programmed to produce such information and convey it to the pulse sequence server 410. For example, during prescans, magnetic resonance data is acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also be employed to process magnetic resonance signals used to detect the arrival of a contrast agent in a magnetic resonance angiography ("MRA") scan. By way of example, the data acquisition server 412 acquires magnetic resonance data and processes it in real-time to produce information that is used to control the scan.

The data processing server 414 receives magnetic resonance data from the data acquisition server 412 and processes it in accordance with instructions downloaded from the operator workstation 402. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 414 are conveyed back to the operator workstation 402 where they are stored. Real-time images are stored in a data base memory cache (not shown in FIG. 4), from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the operator workstation 402. The operator workstation 402 may be used by an operator to archive the images, produce films, or send the images via a network to other facilities.

The MRI system 400 may also include one or more networked workstations 442. By way of example, a networked workstation 442 may include a display 444; one or more input devices 446, such as a keyboard and mouse; and a processor 448. The networked workstation 442 may be located within the same facility as the operator workstation 402, or in a different facility, such as a different healthcare institution or clinic.

The networked workstation 442, whether within the same facility or in a different facility as the operator workstation 402, may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may exchanged between the data processing server 414 or the data store server 416 and the networked workstations 442, such that the data or images may be remotely processed by a networked workstation 442. This data may be exchanged in any suitable format, such as in accordance with the transmission control protocol ("TCP"), the internet protocol ("IP"), or other known or suitable protocols.

In summary, functional mapping based on functional connectivity offers an alternative approach to identifying the functional organization and the abnormality caused by epilepsy and other diseases. This relies on the observation that brain systems exhibit slow spontaneous activity fluctuations that can be measured using fMRI. Demonstrations that intrinsic activity could be used to map the motor system, have been shown, whereby motor areas activated by actual motor movements could be localized using spontaneous activity correlations. The results revealed that the right motor cortex showed strong correlation as well as multiple other regions within the motor system. This approach, often referred to as functional connectivity MRI (fcMRI), has recently been used to study brain systems linked to motor function, vision, audition, memory and attention. While the underlying physiological bases of the slow intrinsic activity fluctuations that underlie fcMRI remain incompletely understood, the measured activity patterns likely reflect a combination of direct and indirect anatomic connectivity.

Several aspects of fcMRI make it a particularly promising tool for identifying functional networks in surgical patients, for instance. First, the procedure is robust in individuals, whereby in typical situations, activation maps can be obtained in roughly 20 minute scan sessions. Second, task compliance is not required, with most fcMRI studies having been conducted during rest and fixation states. However, even that level of task compliance appears unnecessary. fcMRI maps have been obtained during sleep and under anesthesia suggesting that patient compliance will not be required and fcMRI can be performed in a 'task-free' manner. Although preliminary, it seems possible that a single, simple procedure could be used for many functional mapping needs.

Most of the previous findings with fcMRI are based on the normal population. In patients, the pathological change may not only distort cortical anatomy but also the location of functional networks. It is thus of great interest to determine whether fcMRI is applicable for mapping eloquent cortices in patients. If successful, it may offer an extremely powerful approach for pre-surgical evaluation of eloquent cortex which is completely free of tasks.

Mapping of differences in individual brain function is important both in research and clinically, with applications including guided surgery and therapeutic brain stimulation. However, obtaining functional organization of the individual subject's brain involves is exceedingly challenging. In surgical planning, it is desirable to identify the eloquent cortex in individual patients, including motor, language and memory systems. In clinical patients with epilepsy or tumor burdens, not only the cortical anatomy, but also the locations of functional networks are often displaced due to various pathological changes.

To address these challenges, present pre-surgical planning commonly involves multi-layered approaches that include several different procedures and tests. However, these often require a cooperative subject to perform designed tasks, or rely on invasive procedures. In the case of determining functional networks for individual subjects using fMRI, often obtaining robust maps has been limited by poor signal-to-noise, poor reproducibility, and limited ability to map multiple networks at once.

By contrast, the present invention provides a method that overcomes these drawbacks, as well as improving the clinical utility of fMRI, by replacing a series tests with a single non-invasive approach that may quickly map an individual's brain without the need for subject participation. In particular, the present invention makes use of population-level and individual variability information brain networks to map out the functional networks in individual subjects with very high reproducibility within the same subjects, and also very high sensitivity to individual differences. Using an iterative approach that begins with a population information regarding brain parcellation, individual brain characteristics are gradually weighed in by relaxing constraints in relation to the population parcellation, where the weighting is determined using brain network map variability in the large population, as well as the signal-to-noise ratio of the individual data. Thus, the present invention creates a task-free paradigm to map healthy subjects and individuals with abnormal anatomy, such as those suffering from medically intractable epilepsy or brain tumors, allowing for the speedy mapping of neural systems. The algorithm has been tested on a large cohort of normal subjects scanned on several different days and a cohort of surgical pre-operative mapping patients, and results showed good correspondence to those determined by invasive methods, such as electrical cortical stimulation.

The present invention provides a unique approach for use in assessing functional brain organization, which may be implemented in a large population, including children, non-English speaking subjects, developmentally delayed patients, and even patients who are under anesthesia or in a coma, where patient compliance is not required and functional mapping can be performed in a 'task-free' manner. Specifically, the present invention may facilitate investigative efforts, such as identifying intrinsic laterality of multiple functional networks, or mapping eloquent cortices. This may lead to new language and memory lateralization techniques that could replace the traditional Wada test and invasive brain mapping, both of which require a conscious and cooperative patient. Also, the approach of the present invention has the potential for major advance for clinical treatment, for example, in pre-surgical evaluation of epilepsy and tumor patients. Furthermore, the approach of the present invention may be as effective as invasive placement of electrodes (iEEG) in some cases, and may help to guide the placement of grids in others.

Features suitable for combinations and sub-combinations would be readily apparent to persons skilled in the art upon review of the present application as a whole. The subject matter described herein and in the recited claims intends to cover and embrace all suitable changes in technology.

The invention claimed is:

1. A method for producing a functional brain map of a subject, the method comprising:
   i. providing a set of time-series functional magnetic resonance image (fMRI) data acquired from a subject;
   ii. providing a population atlas that associates locations in a population brain to a plurality of functional connectivity networks, the population brain representing a population of subjects;
   iii. providing a variation map indicative of inter-subject variability in the population atlas;
   iv. initializing a subject map using the population atlas, the subject map defining a plurality of functional connectivity networks and indicating locations in a brain of the subject that are assigned to the plurality of functional connectivity networks;
   v. determining a reference signal for each functional connectivity network in the subject map using time-series signals derived from the set of time-series fMRI data;
   vi. computing a plurality of correlation values between the time-series signals derived from the set of time-series fMRI data and each reference signal determined in step (v);
   vii. updating the subject map by reassigning locations in the subject brain based on the computed correlation values;
   viii. updating the reference signal for each functional connectivity network using the updated subject map, the population atlas, the variation map, and the set of fMRI data;
   ix. iteratively repeating steps (vi), (vii) and (viii) until a stopping criterion is satisfied; and
   x. generating a report indicative of a functional brain organization for the brain of the subject using the subject map.

2. The method of claim 1, wherein the method further comprises acquiring the set of time-series fMRI data using a magnetic resonance imaging (MRI) system.

3. The method of claim 1, wherein initializing the subject map comprises projecting the population map onto a model of the subject's brain surface.

4. The method of claim 1, wherein the time-series signals are associated with locations in the brain of the subject.

5. The method of claim 1, wherein determining the reference signal at step (v) comprises averaging the time-series signals from locations assigned to the same functional connectivity network.

6. The method of claim 1, further comprising computing a confidence value defined by a ratio between a first correlation value and a second correlation value, and wherein reassigning the locations at step (vii) is performed in accordance with the confidence value being above a threshold.

7. The method of claim 1, wherein updating the reference signal at step (viii) comprises computing a sum of the reference signal at step (v) and a weighted reference signal determined in dependence of the variation map, a signal-to-noise ratio of the time-series signals, and an iteration number.

8. The method of claim 1, wherein the provided set of time-series fMRI data is indicative of a resting state of the subject.

9. The method of claim 1, wherein the provided set of time-series fMRI data is indicative of a functional task performed by the subject while the time-series fMRI data was acquired.

10. A system for producing functional brain mapping of a subject, the system comprising:
   an input configured to:
      receive a set of time-series functional connectivity magnetic resonance image (fMRI) data acquired from a subject;
      receive a population atlas that associates locations in a population brain to a plurality of functional connectivity networks, the population brain representing a population of subjects;
      receive a variation map indicative of inter-subject variability in the population atlas;
   at least one processor in communication with the input and configured to:
      a. initialize a subject map using the population atlas, the subject map defining a plurality of functional connectivity networks and indicating locations in a brain of the subject that are assigned to the plurality of functional connectivity networks;
      b. determine a reference signal for each functional connectivity network in the subject map using time-series signals derived from the set of time-series fcMRI data;
      c. compute a plurality of correlation values between the time-series signals derived from the set of time-series fMRI data and each determined reference signal;
      d. update the subject map by reassigning locations in the subject brain based on the computed correlation values;
      e. update the reference signal for each functional connectivity network using the updated subject map, the population atlas, the variation map, and the set of fMRI data;
      f. iteratively repeat steps (c), (d) and (e) until a stopping criterion is satisfied;
      g. generate a report indicative of a functional brain organization for the brain of the subject using the subject map; and
   an output configured for displaying the report.

11. The system of claim 10, wherein initializing the subject connectivity map comprises projecting the population map onto a model of the subject's brain surface.

12. The system of claim 10, wherein the time-series signals are associated with locations in the brain of the subject.

13. The system of claim 10, wherein determining the reference signal at step (b) comprises averaging the time-series signals from locations assigned to the same functional connectivity network.

14. The system of claim 10, the at least one processor is further configured to compute a confidence value defined by a ratio between a first correlation value and a second correlation value, and wherein the at least one processor is configured to reassign the locations in the subject brain in accordance with the confidence value being above a threshold.

15. The system of claim 10, wherein the at least one processor is further configured to compute at step (e) a sum of the reference signal from step (b) and a weighted reference signal determined in dependence of the variation map, a signal-to-noise ratio of the time-series signals, and an iteration number.

16. The system of claim 10, wherein received set of time-series fMRI data is indicative of at least one of a resting state of the subject and a functional task performed by the subject while the time-series fMRI data was acquired.

17. A magnetic resonance imaging (MRI) system for producing functional brain mapping of a subject, the system comprising:
   a magnet system configured to generate a polarizing magnetic field about at least a portion of a subject arranged in the MRI system;
   a plurality of gradient coils configured to apply a gradient field to the polarizing magnetic field;
   a radio frequency (RF) system configured to apply a RF excitation field to a brain of the subject, and acquire therefrom a set of time-series functional connectivity magnetic resonance image (fMRI) data;
   at least one computer configured to:
      a. receive a population atlas that associates locations in a population brain to a plurality of functional connectivity networks, the population brain representing a population of subjects;
      b. receive a variation map indicative of inter-subject variability in the population atlas;
      c. initialize a subject map using the population atlas, the subject map defining a plurality of functional connectivity networks and indicating locations in a brain of the subject that are assigned to the plurality of functional connectivity networks;
      d. determine a reference signal for each functional connectivity network in the subject map using time-series signals derived from the set of time-series fcMRI data;
      e. compute a plurality of correlation values between the time-series signals derived from the set of time-series fMRI data and each determined reference signal;
      f. update the subject map by reassigning locations in the subject brain based on the computed correlation values;
      g. update the reference signal for each functional connectivity network using the updated subject map, the population atlas, the variation map, and the set of fMRI data;

h. iteratively repeat steps (e), (f) and (g) until a stopping criterion is satisfied; and i. generate a report indicative of a functional brain organization for the brain of the subject using the subject map.

18. The MRI system of claim 17, wherein initializing the subject connectivity map comprises projecting the population map onto the subject map.

19. The MRI system of claim 17, wherein the time-series signals are associated with locations in the brain of the subject.

20. The MRI system of claim 17, wherein determining the reference signal at step (b) comprises averaging the time-series signals from locations assigned to the same functional connectivity network.

21. The MRI system of claim 17, the at least one computer is further configured to compute a confidence value defined by a ratio between a first correlation value and a second correlation value and wherein the computer system is configured to reassign the locations in the subject map in accordance with the confidence value being above a threshold.

22. The MRI system of claim 17, wherein the at least one processor is further configured to compute at step (g) a sum of the reference signal from step (d) and a weighted reference signal determined in dependence of the variation map, a signal-to-noise ratio of the time-series signals, and an iteration number.

23. The MRI system of claim 17, wherein received set of time-series fMRI data is indicative of at least one of a resting state of the subject and a functional task performed by the subject while the time-series fMRI data was acquired.

* * * * *